United States Patent
Popovic

(10) Patent No.: US 9,750,399 B2
(45) Date of Patent: Sep. 5, 2017

(54) REAL-TIME DEPTH ESTIMATION FROM MONOCULAR ENDOSCOPE IMAGES

(75) Inventor: Aleksandra Popovic, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 573 days.

(21) Appl. No.: 13/266,465

(22) PCT Filed: Mar. 25, 2010

(86) PCT No.: PCT/IB2010/051316
§ 371 (c)(1),
(2), (4) Date: Oct. 27, 2011

(87) PCT Pub. No.: WO2010/125481
PCT Pub. Date: Nov. 4, 2010

(65) Prior Publication Data
US 2012/0056986 A1    Mar. 8, 2012

Related U.S. Application Data

(60) Provisional application No. 61/173,722, filed on Apr. 29, 2009.

(51) Int. Cl.
*A61B 1/00* (2006.01)
*A61B 1/04* (2006.01)
(Continued)

(52) U.S. Cl.
CPC ............ *A61B 1/04* (2013.01); *A61B 1/00009* (2013.01); *A61B 1/313* (2013.01); *A61B 5/065* (2013.01);
(Continued)

(58) Field of Classification Search
CPC ... A61B 1/00193; A61B 1/04; A61B 1/00009; A61B 1/00096; A61B 1/00172;
(Continued)

(56) References Cited

U.S. PATENT DOCUMENTS 4,574,199 A * 3/1986 Pryor ..................... 250/559.33
5,243,665 A * 9/1993 Maney et al. ............. 382/152
(Continued)

FOREIGN PATENT DOCUMENTS

| CN | 101271578 A | 9/2008 |
|----|-------------|--------|
| EP | 2030558 | 3/2009 |

(Continued)

OTHER PUBLICATIONS

Seon-Yeong et al. "3D depth estimation for target region using optical flow and mean-shift algorithm," Control, Automation and Systems, 2008. ICCAS 2008. International Conference on , vol., no., pp. 34,39, Oct. 14-17, 2008.*

(Continued)

*Primary Examiner* — Frank Huang

(57) ABSTRACT

An endoscopic surgical method involves an advancement of an endoscope (20) to a target location within an anatomical region of a body and a generation of a plurality of endoscopic video frames (22) as the endoscope (20) is advanced to the target location with the endoscopic video frames (2) illustrating monocular endoscopic images of the anatomical region. For real-time estimation of a depth of an object within monocular endoscopic images (e.g., depth of a bronchial wall within an monocular endoscopic images of a bronchial tube), the method further involves (S41) a determination of an optical flow of one or more image points within a frame time series of the monocular endoscopic images of the anatomical region, and (S42) an estimation of a depth field indicative of a depth of the object within the (Continued)

monocular endoscopic images as a function of the optical flow of the image point(s).

12 Claims, 4 Drawing Sheets

(51) Int. Cl.
| | | |
|---|---|---|
| *A61B 1/313* | (2006.01) | |
| *A61B 5/06* | (2006.01) | |
| *A61B 34/20* | (2016.01) | |
| *A61B 90/00* | (2016.01) | |

(52) U.S. Cl.
CPC ......... *A61B 34/20* (2016.02); *A61B 2090/061* (2016.02)

(58) Field of Classification Search
CPC ......... A61B 1/041; A61B 1/07; A61B 5/0062; A61B 19/00; A61B 1/3132; A61B 19/2203; A61B 19/5244; H04N 13/0239; H04N 2005/2255; G06F 19/00; G06F 19/3418; G06F 19/348; B25J 9/1689; G06K 9/00624
USPC .......................................................... 348/45
See application file for complete search history.

(56) References Cited

U.S. PATENT DOCUMENTS

| | | | | |
|---|---|---|---|---|
| 5,920,394 | A * | 7/1999 | Gelbart et al. ................. | 356/615 |
| 6,135,946 | A | 10/2000 | Konen et al. | |
| 6,384,859 | B1 | 5/2002 | Matsumoto et al. | |
| 8,422,741 | B2 | 4/2013 | Eggert et al. | |
| 8,535,336 | B2 * | 9/2013 | Trovato ........................ | 606/130 |
| 2002/0156345 | A1 | 10/2002 | Eppler et al. | |
| 2004/0022419 | A1 | 2/2004 | Kesaniemi | |
| 2004/0109585 | A1 | 6/2004 | Tao et al. | |
| 2005/0017967 | A1 * | 1/2005 | Ratti et al. .................... | 345/418 |
| 2005/0084135 | A1 | 4/2005 | Chen | |
| 2005/0272999 | A1 | 12/2005 | Guendel | |
| 2006/0020562 | A1 | 1/2006 | Murali | |
| 2006/0227210 | A1 * | 10/2006 | Raab et al. .................... | 348/139 |
| 2006/0235671 | A1 | 10/2006 | Kirchberg et al. | |
| 2007/0015997 | A1 | 1/2007 | Higgins et al. | |
| 2007/0055128 | A1 | 3/2007 | Glossop | |
| 2007/0167714 | A1 | 7/2007 | Kiraly et al. | |
| 2007/0274577 | A1 | 11/2007 | Font-Reaulx-Rojas | |
| 2008/0058593 | A1 | 3/2008 | Gu et al. | |
| 2008/0106669 | A1 | 5/2008 | Tsai et al. | |
| 2008/0207997 | A1 * | 8/2008 | Higgins ............. | A61B 1/00009 600/114 |
| 2008/0262312 | A1 * | 10/2008 | Carroll et al. ................. | 600/160 |
| 2009/0048482 | A1 | 2/2009 | Hong et al. | |
| 2009/0088634 | A1 * | 4/2009 | Zhao et al. .................... | 600/427 |
| 2012/0056986 | A1 | 3/2012 | Popovic | |
| 2012/0327221 | A1 * | 12/2012 | Christoph et al. ............. | 348/135 |

FOREIGN PATENT DOCUMENTS

| | | |
|---|---|---|
| JP | H07162845 A | 6/1995 |
| JP | H07234935 A | 9/1995 |
| JP | 2003290131 A | 10/2003 |
| KR | 100234196 B1 | 12/1999 |
| WO | WO2007008289 | 1/2007 |
| WO | WO2007042986 | 4/2007 |
| WO | WO2007059233 | 5/2007 |
| WO | WO2008032230 | 3/2008 |
| WO | WO2009088634 | 7/2009 |
| WO | WO 2009/156892 A1 * | 12/2009 |

OTHER PUBLICATIONS

Liu, et al. "A stable optic-flow based method for tracking colonoscopy images." Computer Vision and Pattern Recognition Workshops, 2008. CVPRW'08. IEEE Computer Society Conference on. IEEE, 2008.*

Shinagawa et al., "Virtual Bronchoscopic Navigation System shortens the Examiner time—Feasibility Study of Virtual Bronchoscopic Navigation System", Science Direct, Lunc Cancer, vol. 56, Issue 2, May 2001, pp. 201-206.

Nappi et al., "Virtual Endoscopic Visualization of the Colon by Shape-Scale Signatures" (Abstract), IEEE, one page.

Twardowski et al., "Fast Estimation of Broncho-Fiberscope Egomotion for CT-Guided Transbronchial Biopsy", IEEE Int. Conf. Image Processing, Atlanta, pp. 1189-1192.

Zhang Shufang, "Approach to Image Sequences Analysis based on Sparse Optical Flow Field", China Doctoral Dissertations & Master Theses Full Text, Database Master of Information Technology, vol. 1, (2005), pp. 1-61.

Wu, C.H. et al. "Three-Dimensional Modeling from endoscopic video using geometric constraints via feature positioning", IEEE Transactions on Biomedical Engineering, vol. 54, No. 7, Jul. 2007.

Shin, B.S. et al. "An efficient navigation method for virtual endoscopy using volume ray casting", Computational Sicence—ICCS 2003, PT III, Proceedings Book Series: Lecture Notes in Computer Science Volume: 2659 pp. 60-69 Published: 2003.

* cited by examiner

REAL-TIME DEPTH ESTIMATION FROM MONOCULAR ENDOSCOPE IMAGES

The present invention generally relates to minimally invasive surgeries involving an endoscope. The present invention specifically relates to estimating real-time depth of objects shown in images obtained from an endoscope.

Generally, a minimally invasive surgery utilizes an endoscope, which is a long, flexible or rigid tube having an imaging capability. Upon insertion into a body through a natural orifice or a small incision, the endoscope provides image of the region of interest that may be viewed through an eyepiece or on a screen as a surgeon performs the operation. Essential to the surgery is the depth information of object(s) within the images that will enable the surgeon to be able to advance the endoscope while avoiding the object(s) and will facilitate a real-time tracking position of the endoscope. However, the frames of an endoscopic image are two-dimensional and the surgeon therefore may lose the perception of the depth of object(s) viewed in the screen shoot of the images.

The present invention provide a technique that utilizes endoscopic video frames from the monocular endoscopic images to generate a depth map despite the two-dimensional limitation of the endoscopic video frames.

One form of the present invention is a minimally invasive surgical system employing an endoscope and an endoscopic surgical control unit. In operation, the endoscope generates a plurality of endoscopic video frames as the endoscope is advanced to a target location within an anatomical region of a body with the endoscopic video frames illustrating a monocular endoscopic images of the anatomical region. For real-time estimation of a depth of an object within monocular endoscopic images (e.g., shape of a bronchial wall within monocular endoscopic images of a bronchial tube), the endoscopic surgical control unit receives the endoscopic video frames as the endoscope is advanced to the target location to estimate a depth field indicative of a depth of the object within the monocular endoscopic images of the anatomical region as a function of an optical flow of the image point(s) within a frame time series of the monocular endoscopic images of the anatomical region.

A second form of the present invention is an endoscopic surgical method involving an advancement of an endoscope to a target location within an anatomical region of a body and a generation of a plurality of endoscopic video frames as the endoscope is advanced to the target location with the endoscopic video frames illustrating monocular endoscopic images of the anatomical region. For real-time estimation of a depth of an object within monocular endoscopic images (e.g., shape of a bronchial wall within an monocular endoscopic images of a bronchial tube), the method further involves a generation of an optical flow of one or more image points within a frame time series of the monocular endoscopic images of the anatomical region, and an estimation of a depth field indicative of a depth of the image point(s) within the monocular endoscopic images as a function of the optical flow of the image point(s).

FIG. 1. illustrates an exemplary embodiment of a minimally invasive surgical system in accordance with the present invention.

Figure 1:
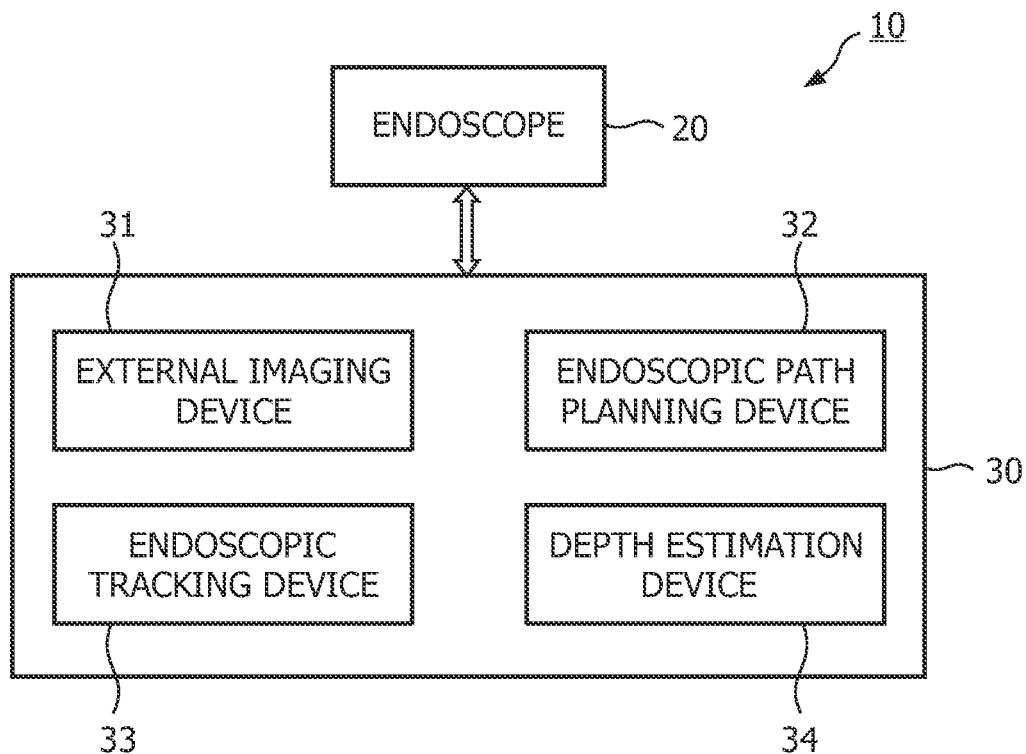

As shown in FIG. 1, a minimally invasive surgical system 10 of the present invention employs an endoscope 20 and a endoscopic surgical control unit 30.

Endoscope 20 is broadly defined herein as any device structurally configured for internally imaging an anatomical region of a body (e.g., human or animal) via fiber optics, lenses, miniaturized (e.g. CCD based) imaging systems or the like. Examples of endoscope 20 include, but are not limited to, any type of scope (e.g., a bronchoscope, a colonoscope, a laparoscope, etc.) and any device similar to a scope that is equipped with an image system (e.g., an imaging cannula).

An external imaging device 31 of unit 30 is broadly defined herein as any device structurally configured for externally imaging an anatomical region of a body. Examples of external imaging device 31 include, but are not limited to, a computer tomography device, a magnetic resonance imaging device, an ultrasound device and an x-ray device.

An endoscopic path planning device 32 of unit 30 is broadly defined herein as any device structurally configured for pre-operatively planning a kinematic path to reach a target location within an anatomical region of a body for purposes of configuring endoscope 20 (e.g., configuring an imaging cannula) and/or for purposes of controlling endoscope 20 in reaching the target location (e.g., operating the controls of a bronchoscope). In the context of endoscope 20 being a bronchoscope or a kinematically similar scope, a path planning technique taught by International Application WO 2007/042986 A2 to Trovato et al. published Apr. 17, 2007, and entitled "3D Tool Path Planning, Simulation and Control System" may be used by device 32 to generate a kinematically correct path for endoscope 20 within the anatomical region of the body (e.g., lungs) as indicated by a 3D dataset of the anatomical region as acquired by external imaging device 31. In the context of endoscope 20 being an imaging nested cannula or a kinematically similar device, the path planning/nested cannula configuration technique taught by International Application WO 2008/032230 A1 to Trovato et al. published Mar. 20, 2008, and entitled "Active Cannula Configuration For Minimally Invasive Surgery" may be used by device 32 to generate a kinematically correct configuration for endoscope 20 for reaching the target location within the anatomical region of the body (e.g., lungs) as indicated by a 3D dataset of the anatomical region as acquired by external imaging device 31.

An endoscopic tracking device 33 of unit 30 is broadly defined herein as any device structurally configured for tracking a position of endoscope 20 within an anatomical region of a body. One example of endoscopic tracking device 33 is the image-based tracking unit taught by U.S.

Provisional Patent Application 61/106,669 to Trovato et al. filed Oct. 20, 2008 and entitled "Image-Based Localization Method and System." Another example of endoscopic tracking device 33 is the optical tracking device taught by U.S. Pat. No. 6,135,946 to Konen et al. issued Oct. 4, 2004, and entitled "Method and System for Image-Guided Interventional Endoscopic Procedures". A further example of endoscopic tracking device 33 is any commercially available electromagnetic tracking unit, such as, for example, the electromagnetic tracking unit commercially available as the inReach™ system from superDimension, Inc.

Depth estimation device 34 of unit 30 is broadly defined herein as any device structurally configured for estimating a depth field from a pattern of actual motion of image points/features in a frame time series acquired by endoscope 20 (i.e., two or more images in accordance with any type of time sequence). In practice, depth estimation device 34 may be utilized by unit 30 for estimating a depth field to facilitate endoscopic path planning device 32 in generating a pre-operative configuration of endoscope 20 to reach a target location within an anatomical region and/or in generating a pre-operative plan of a kinematic path for controlling endoscope 20 in reaching the target location. Additionally, depth estimation device 34 may be utilized in practice by unit 30 for estimating a depth field to facilitate a registration of the endoscopic image from endoscope 20 with the pre-operative images acquired by device 31 and/or to enhance a real-time tracking of a position of endoscope 20 within the anatomical region as endoscope 20 is advanced to the target location. Further, in practice, depth estimation device 34 may operate independently of other devices from unit 30 or be internally incorporated within one of the other devices of unit 30.

Figure 2:
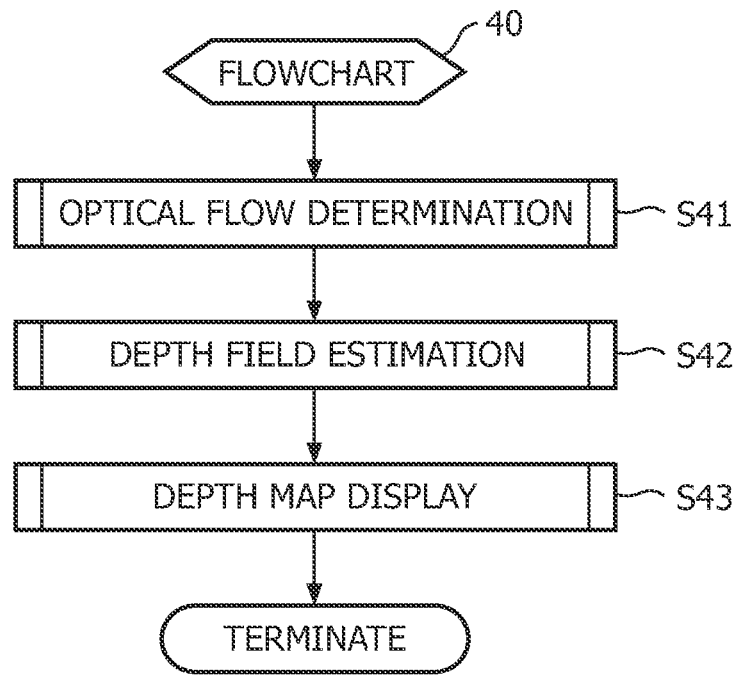
FIG. 2 illustrates a flowchart representative of an exemplary embodiment of a depth estimation method in accordance with the present invention.

Flowchart 40 as shown in FIG. 2 represents a depth estimation method of the present invention as executed by depth estimation device 34 (FIG. 1). For this method, depth estimation device 34 begins with a stage S41 of flowchart 40 to determine an optical flow of motion of image points/features in a frame time series of monocular endoscopic images acquired by endoscope 20. Subsequently or concurrently with the execution of stage S41, depth estimation device 34 proceeds to a stage S42 of flowchart 40 to estimate a depth field from the optical flow where the depth field indicates the depth of one or more objects in the monocular endoscopic images and the depth field estimation is utilized for the display of a depth map in a stage S43 of flowchart 40.

Figure 3:
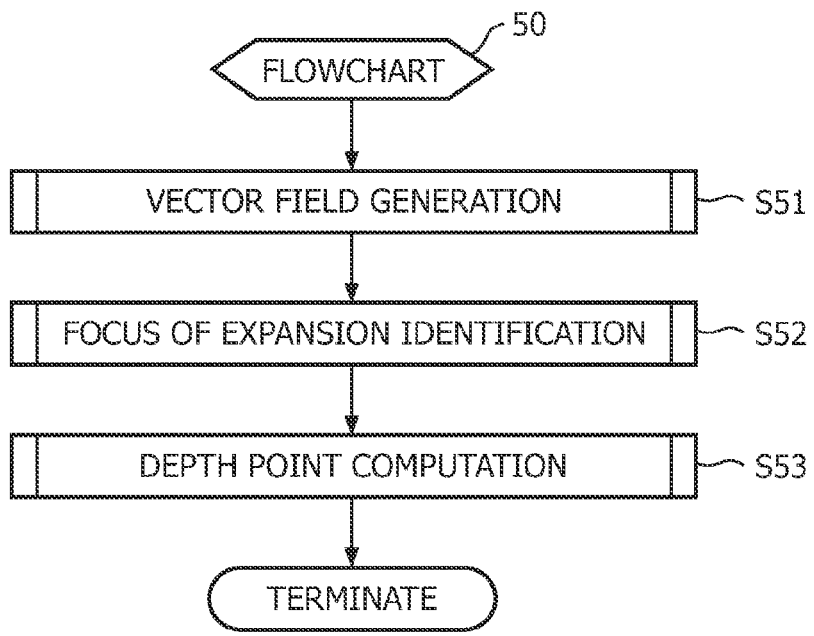
FIG. 3 illustrates a flowchart representative of a first exemplary embodiment of the depth estimation method illustrated in FIG. 2 in accordance with the present invention.
Figure 4:
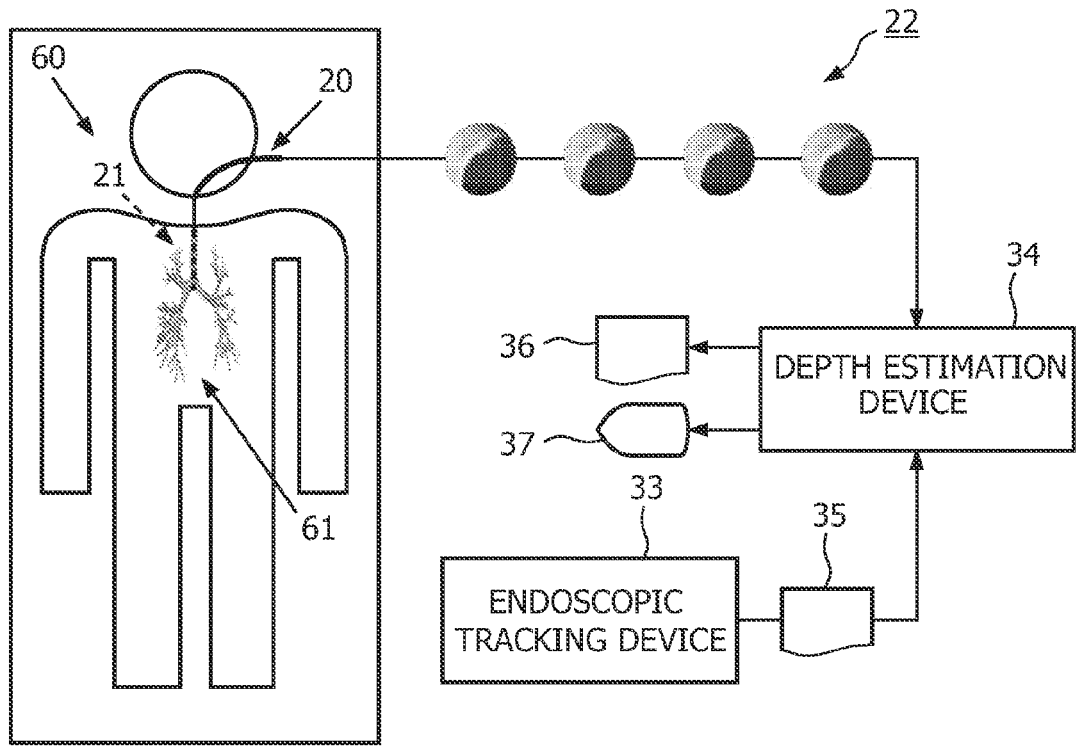
FIG. 4 illustrates an exemplary application of the flowchart illustrated in FIG. 3.
Figure 5:
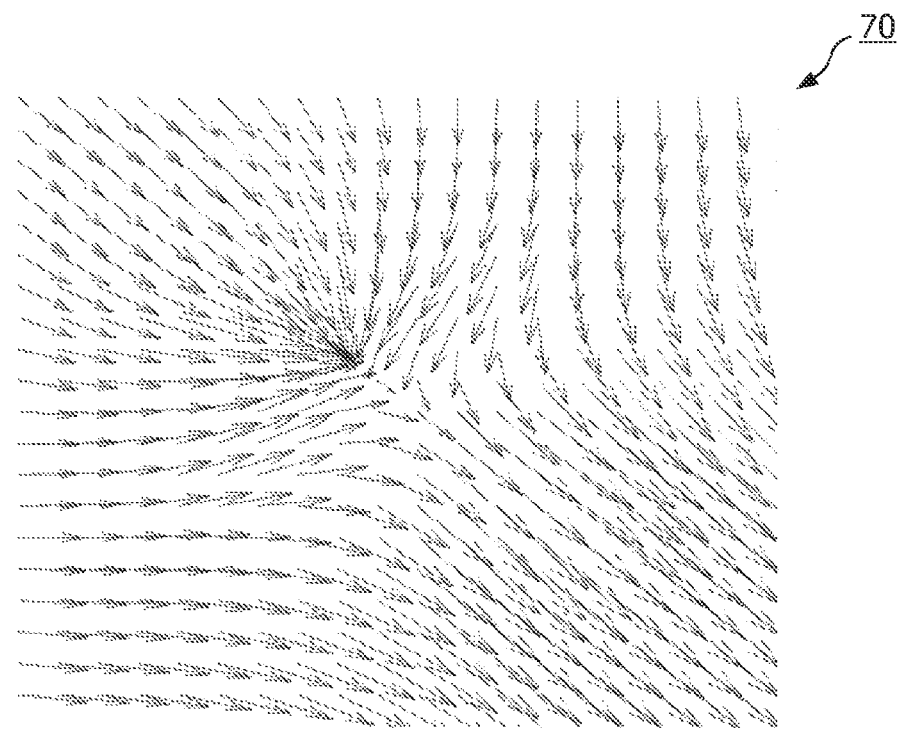
FIG. 5 illustrates an exemplary optical flow as known in the art.

Flowchart 50 as shown in FIG. 3 represents an exemplary embodiment of flowchart 40 (FIG. 2). Specifically, the determination of the optical flow by device 34 involves a generation of a vector field including a plurality of vectors during a stage S52 of flowchart 50 with each vector representing a motion of a particular image point within the monocular endoscopic images (e.g., between two monocular endoscopic images). For example, as shown in FIG. 4, an optical flow of motion of image points/features for each endoscopic video frame in a frame time series 22 of bronchial tubes 61 of a patient 60 taken by endoscope 20 as endoscope 20 traverses an endoscopic path 21 within bronchial tubes 61 may be determined by vectors representing a motion of image points within the monocular endoscopic images (e.g., a vector field 70 as shown in FIG. 5).

Furthermore, a velocity of endoscope 20 between two endoscopic video frames may be computed from relative positions of endoscope 20 for the given frames as tracked by endoscopic tracking device 33. The frames may be consecutive or at some delay in view of an assumption of a stationary object being observed by endoscope 20 between frames. Given the velocity of endoscope 20, a depth field may be estimated from a point on the optical flow that is not moving in consecutive slices that is known as a focus of expansion ("FOE") in view of the fact that an optical axis of endoscope 20 is aligned with its movement and therefore the FOE is aligned with the movement of endoscope 20. Depth information for each point may be computed by knowing (1) a distance D of every point from the FOE as identified by a stage S52 of flowchart 50, (2) an amplitude V of optical flow in every point and (3) a velocity v of endoscope 20. Specifically, depth estimation device 34 computes depth information for each image point during a stage S53 of flowchart 50 in accordance with the following equation [1]:

$$Z = v*D/V \qquad [1]$$

where Z is depth of an image point. In this case, the X and Y positions may be computed from intrinsic parameters of endoscope 20 (e.g., a focal point, etc).

Figure 6:
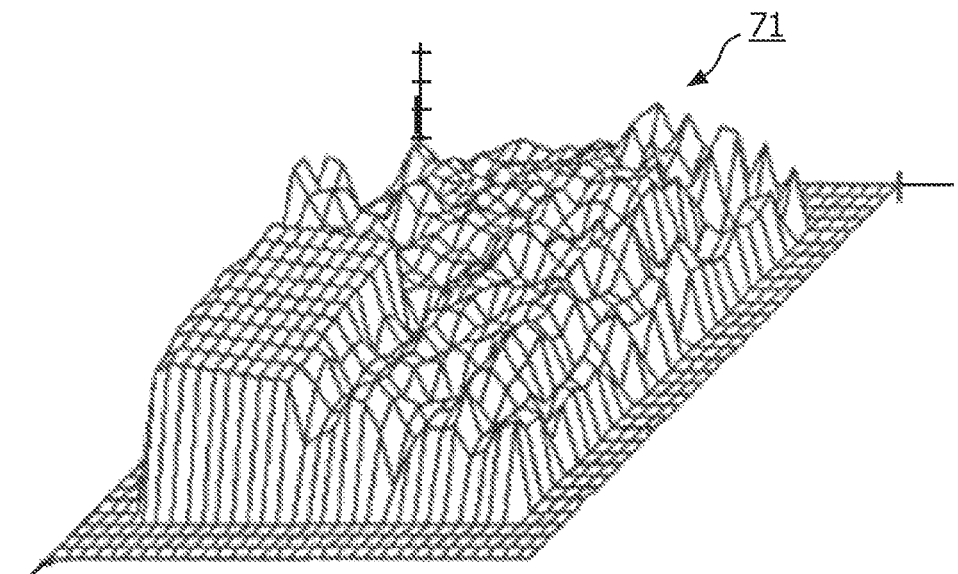
FIG. 6 illustrates an exemplary depth field as known in the art.
Figure 7:
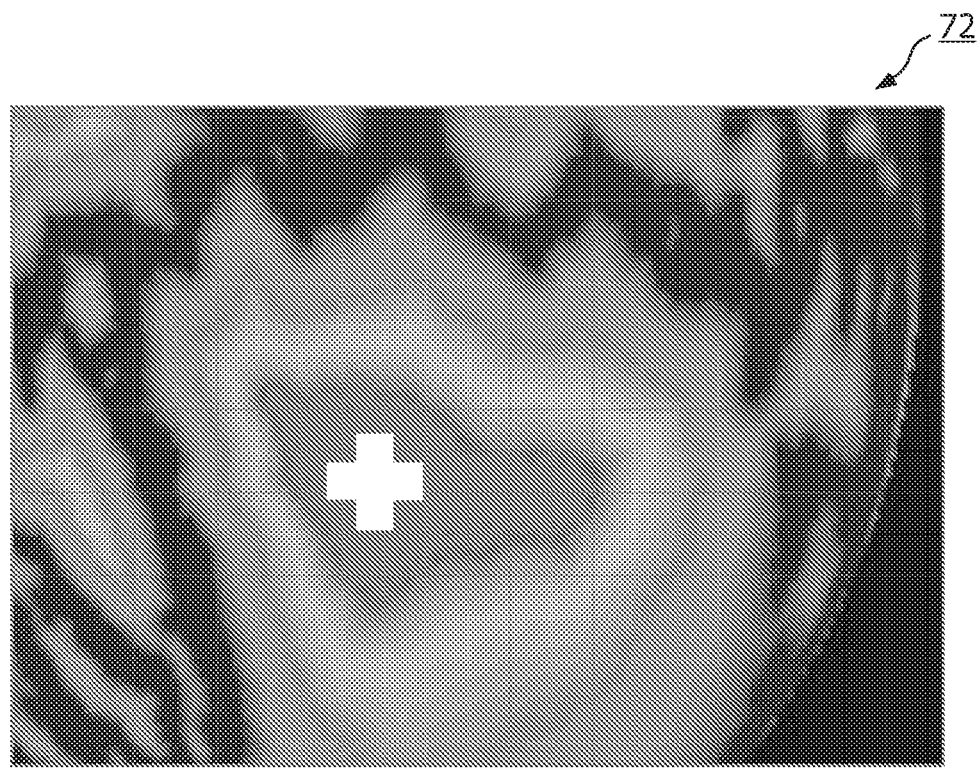
FIG. 7 illustrates an exemplary depth map as known in the art.

For example, as shown in FIG. 4, endoscopic tracking device 33 provides tracking data 35 to depth estimation device 34 that enables depth estimation device 34 to determine the velocity v of endoscope 20 in generating frame time series 23. As such, based on knowing the distance D of every image point from the identified FOE in the vector field and an amplitude V of optical flow in every point, depth estimation device 34 computes the Z depth for each point within a computed vector field of frame time series 23 to estimate a depth field 36 (e.g., a depth field 71 shown in FIG. 6) and to generate a depth map 37 (e.g., color coded depth field 72 shown in FIG. 7).

Figure 8:
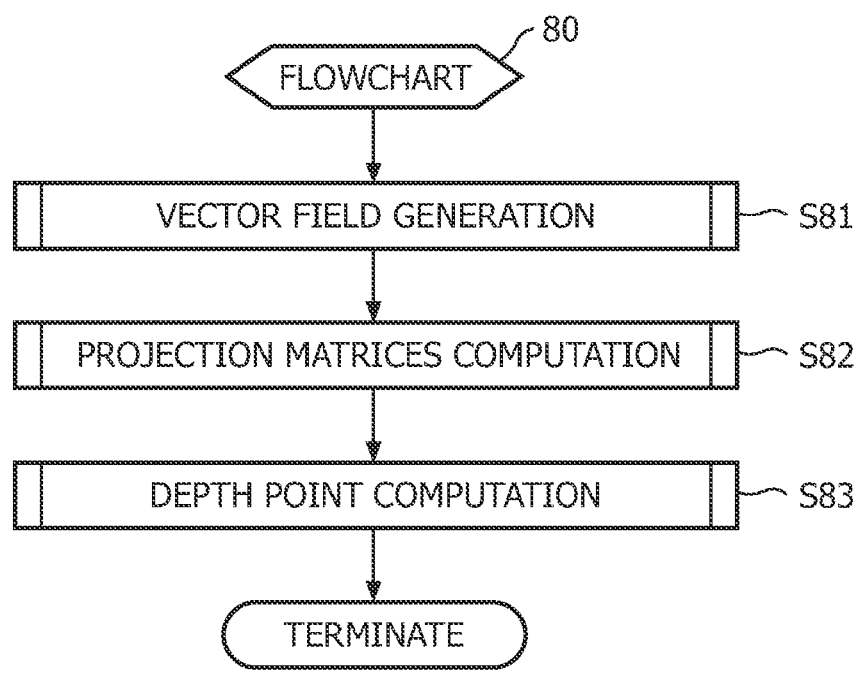
FIG. 8 illustrates a flowchart representative of a second exemplary embodiment of the depth estimation method illustrated in FIG. 2 in accordance with the present invention.

Flowchart 80 as shown in FIG. 8 represents an alternative embodiment of flowchart 40 (FIG. 2). Flowchart 80 is based on a stereoscopic vision of two views of the same scene (i.e., two endoscopic video frames taken at slightly different time). Specifically, upon generation of the vector field during a stage S81 of flowchart 80 and given that the endoscope 20 is being tracked by device 33, relative positions of endoscope 20 for two views are also known. For this case, a coordinate system is attached to the camera pose creating the first view. Therefore, a known pose that generated the second view relative to the first view is defined with 3×3 rotation matrix R and 3×1 translation vector t. Furthermore, a camera intrinsic 3×3 matrix K may be defined given that intrinsic camera parameters of endoscope 20 are known (e.g., from a camera datasheet or from a known calibration method). From these data, a stage S82 of flowchart 80 involves a computation of 4×4 projection matrices for the first view P1 and the second view P2 in accordance with the following equations [2] and [3]:

$$P_1 = [I|0] \qquad [2]$$

$$P_2 = K*[R|T]*K^{-1} \qquad [3]$$

A stage S83 of flowchart 80 involves a geometric triangulation of the projection elements of the projection matrices to compute the depth of each image point.

If endoscope 20 is not tracked by device 33, a similar procedure may be performed using the vector field to estimate projection matrices. In this case, the depth would be estimated to a scale factor only, real physical depth would not be known.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A minimally invasive surgical system, comprising:
a monocular endoscope, having an optical axis, for generating a plurality of endoscopic video frames as the monocular endoscope is advanced along the optical axis of the monocular endoscope to a target location within an anatomical region of a body, the endoscopic video frames illustrating monocular endoscopic images of the anatomical region; and
an endoscopic surgical control unit in communication with the endoscope to receive the endoscopic video frames as the endoscope is advanced to the target location,
wherein the endoscope surgical control unit is operable to track positions of the endoscope within the anatomical region as the endoscope is advanced to the target location within the anatomical region,
wherein the endoscopic surgical control unit is operable to estimate a depth field indicative of a depth of an object within the monocular endoscopic images of the anatomical region as a function of an optical flow of at least one image point within a frame time series of the monocular endoscopic image of the anatomical region and the tracked positions of the endoscope within the anatomical region, and
wherein the endoscopic surgical control unit is operable to determine the optical flow by generating a vector field including a plurality of vectors, each vector indicative of a motion of one of the image points within the frame time series.

2. The minimally invasive surgical system of claim 1, wherein the endoscopic surgical control unit is further operable to generate a depth map display representative of a depth field estimation.

3. The minimally invasive surgical system of claim 1, wherein the endoscopic surgical control unit is further operable to register the monocular endoscopic images with a pre-operative image of the anatomical region of the body as a function of the depth field estimation.

4. The minimally invasive surgical system of claim 1, wherein the endoscopic surgical control unit is further operable to pre-operatively plan a kinematic path for the endoscope to reach the target location within the anatomical region.

5. The minimally invasive surgical system of claim 1, wherein the endoscope is one of a group including a bronchoscope and a nested cannula.

6. An endoscopic surgical method, comprising:
advancing a monocular endoscope to a target location within an anatomical region of a body;
generating a plurality of endoscope video frames as the monocular endoscope is advanced along a focal axis of the monocular endoscope to the target location, the endoscopic video frames illustrating monocular endoscopic images of the anatomical region;
tracking positions of the endoscope within the anatomical region as the monocular endoscope is advanced to the target location within the anatomical region;
determining an optical flow of at least one image point within a frame time series of the monocular endoscopic images of the anatomical region; and
estimating a depth field indicative of a depth of an object within the monocular endoscopic images as a function of the optical flow and the tracked positions of the endoscope within the anatomical region;
wherein the step of determining the optical flow includes generating a vector field including a plurality of vectors, each vector indicative of a motion of one of the image points within the frame time series.

7. The endoscopic surgical method of claim 6, wherein the estimation of the depth field includes:
identifying a focus of expansion within the vector field; and
computing a depth point for each image point as a function of a distance of each image point from the focus of expansion.

8. The endoscopic surgical method of claim 6, wherein the estimation of the depth field includes:
computing a depth point for each image point as a function of an amplitude of each vector in the vector field.

9. The endoscopic surgical method of claim 6, wherein the estimation of the depth field includes:
computing a depth point for an image point as a function of a velocity of each vector in the vector field.

10. The endoscopic surgical method of claim 6, wherein the estimation of the depth field includes:
computing projection matrices as a function of the vector field.

11. An endoscopic surgical method, comprising;
advancing a monocular endoscope to a target location within an anatomical region of a body;
generating a plurality of endoscope video frames as the monocular endoscope is advanced along a focal axis of the monocular endoscope to the target location, the endoscopic video frames illustrating monocular endoscopic images of the anatomical region;
determining an optical flow of at least one image point within frame time series of the monocular endoscopic images of the anatomical region; and
estimating a depth field indicative of a depth of an object within the monocular endoscope images as a function of the optical flow,
wherein the determination of the optical flow includes generating a vector field including a plurality of vectors, each vector indicative of a motion of one of the image points within the frame time series, and
wherein the estimation of the depth field includes computing projecting matrices as a function of the vector field, and computing a depth point for each image point as a function of a geometric triangulation of projection elements of the projection matrices.

12. The endoscopic surgical method of claim 6, further comprising:
displaying a depth map representative of the depth field estimation.

* * * * *